US00PP34001P2

(12) United States Plant Patent
Van Swieten

(10) Patent No.: US PP34,001 P2
(45) Date of Patent: Mar. 8, 2022

(54) *PHALAENOPSIS* ORCHID PLANT NAMED 'PHA1734832'

(50) Latin Name: ***Phalaenopsis* hybrid**
Varietal Denomination: PHA1734832

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,581

(22) Filed: Aug. 25, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

CPVO hit on a *Phalaenopsis* plant namd, 'PHA1734832', having UPOV code QZ PBR 2020/2294, filed Sep. 22, 2020.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHA1734832', particularly characterized by having light greenish-yellow, shaded flowers with yellow and white lips, flowers that are flat in lateral view, about 12 leaves, apical lobes that are dotted at the base, and is propagated by meristem tissue culture, is disclosed.

3 Drawing Sheets

Genus and species: *Phalaenopsis* hybrid.
Variety denomination: 'PHA1734832'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA1734832'.

The new *Phalaenopsis* plant is a product of a planned breeding program conducted by the inventor in Bleiswijk, the Netherlands. The objective of this breeding program was to create a new *Phalaenopsis* plant with light greenish-yellow, shaded flowers with yellow and white lips, suitable for potted plant production.

The new *Phalaenopsis* plant 'PHA1734832' is a result of cross-pollination made by the inventor in August 2013 in Bleiswijk, the Netherlands, of the proprietary female, or seed parent, *Phalaenopsis* hybrid '33350-01' (unpatented) with the proprietary male, or pollen parent, *Phalaenopsis* hybrid '42375-01' (unpatented).

The new *Phalaenopsis* was selected by the inventor as a single plant within the progeny of the stated cross-pollination in a controlled greenhouse in Bleiswijk, the Netherlands, in July 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 22, 2020 (Application no. 2020/2294), by Applicant who obtained the subject matter disclosed directly from the inventor. 'PHA1734832' has not been made publicly available or sold anywhere in the world prior to the effective filing date of this application with the exception of sales or disclosures made one year or less before the effective filing date of this claimed invention by Applicant who obtained 'PHA1734832' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA1734832' as a new and distinct variety of *Phalaenopsis* plant:

1) Light greenish-yellow, shaded flowers with yellow and white lips;
2) Flower shape in lateral view is flat;
3) Plant has about 12 leaves; and
4) Apical lobe is dotted at the base.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in July 2021. Colors in the photographs may differ from the color values cited in the detailed botanical description, which accurately describe the actual colors of the new variety.

DESCRIPTION OF THE NEW VARIETY

Figure 1:
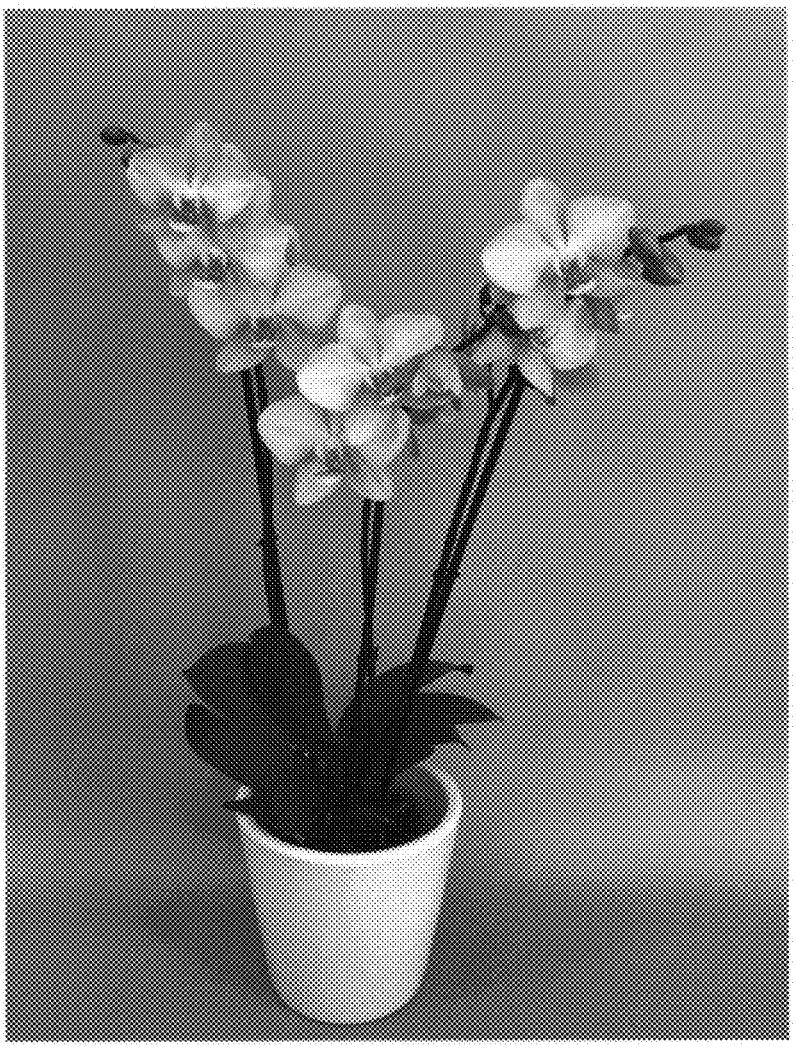
FIG. 1 shows the overall plant habit, including blooms, buds, and foliage of 'PHA1734832'.
Figure 2:
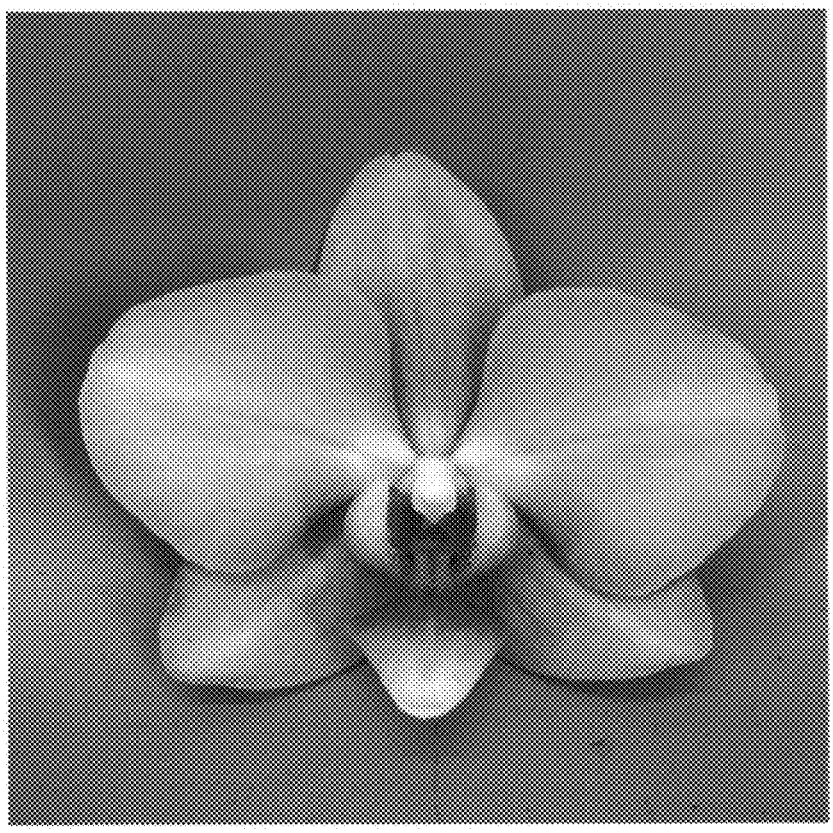
FIG. 2 shows a close-up of a flower of 'PHA1734832'.
Figure 3:
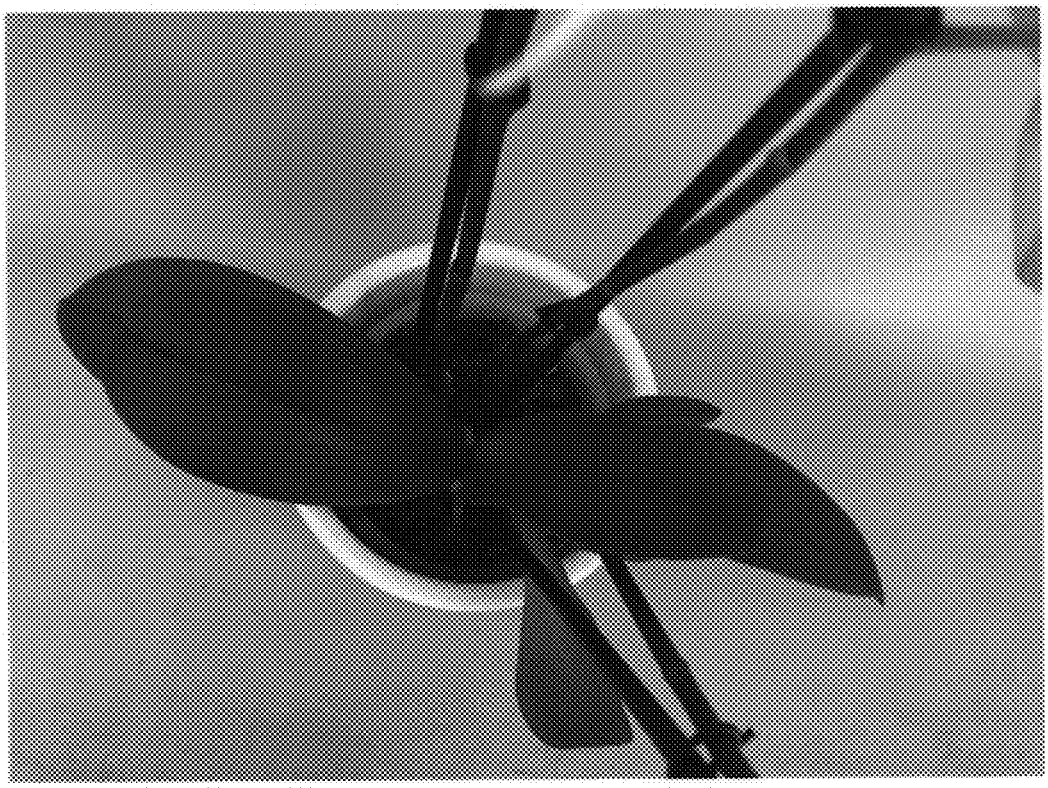
FIG. 3 shows an overhead view of the leaves of 'PHA1734832'.

The following detailed description sets forth the distinctive characteristics of 'PHA1734832'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in July 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHA1734832'.

Parentage:

*Female parent.*—*Phalaenopsis* cultivar '33350-01' (unpatented).

*Male parent.*—*Phalaenopsis* cultivar '42375-01' (unpatented).

Propagation:

*Type.*—Meristem tissue culture.

Roots:

*Root description.*—Greyed-green (a color in between RHS 190B and RHS 190C) colored roots with branching lateral roots having yellow-green (a color in between RHS 144B and RHS 144C) colored root tips.

Plant:

*Crop time to flowering.*—Following asexual propagation (in vitro), the rooted cuttings grow for 20-24 weeks. After transplantation into 12-cm pots, the plants are finished after 48 to 50 weeks.

*Growth habit of the peduncle.*—Upright to slightly pendent with raceme and panicle inflorescence.

*Height (from soil level to top of inflorescence).*—Approximately 42.0 cm to 47.0 cm.

*Width (measured from leaf tips).*—About 28.0 cm to 31.0 cm.

*Vigor.*—Strong.

Leaves:

*Mature leaves.*—Quantity per plant: 11 to 12 leaves are produced before flowering. Length (fully expanded): 13.0 cm to 16.0 cm. Width: 5.5 cm to 6.5 cm. Position of the broadest part of the leaf: Toward apex. Shape: Obovate. Base shape: Moderately elongated. Apex: Obtuse unequal. Leaf blade angle with the petiole (measured from the horizontal position): Between 20 degrees and 35 degrees. Leaf margin: Entire. Color: Upper surface: A color in between RHS 146A and RHS 147A with a brown margin (RHS 200C). Lower surface: Green (RHS 146B) with reddish-brown margin (RHS 200B) and purple overcolor (RHS N77A). Texture (both upper and lower surfaces): Smooth. Thickness: 1.8 mm to 2.2 mm. Variegation: Absent. Venation: Pattern: Parallel. Color of the midvein: Upper surface: RHS 147A. Lower surface: RHS N79B.

Peduncle:

*Quantity per plant.*—1 to 3.

*Number of flowers per peduncle.*—8 to 11.

*Length.*—42.0 cm to 47.0 cm.

*Diameter.*—5.0 mm to 6.0 mm.

*Strength.*—Strong.

*Aspect.*—Upright to slightly pendent.

*Texture.*—Smooth.

*Color.*—Reddish-brown-purple (a color in between RHS N200A and RHS N77A) with a touch of yellow-green (RHS 146D).

*Internode length.*—1.5 cm to 2.5 cm.

Inflorescence description:

*Appearance.*—Upright to slightly pendent, raceme and panicle inflorescence with bilaterally symmetrical flowers that open in succession beginning with the lowermost flower.

*Number of inflorescences.*—1 to 3.

*Inflorescence size.*—Height (from base to tip): 150.0 mm to 180.0 mm.

*Flowering time.*—First flowers can be expected 10 to 11 months after planting in a 12-cm pot.

*Flower.*—Height: 75.0 mm to 80.0 mm. Diameter: 85.0 mm to 90.0 mm. Depth of lip: 18.0 mm to 20.0 mm.

*Flower shape.*—Flat.

*Flower longevity.*—On the plant: 12 to 14 weeks.

*Fragrance.*—Absent.

*Flower bud.*—Average size: Medium to large. Length: 22.0 mm to 24.0 mm. Width: 17.0 mm to 19.0 mm. Shape: Egg shaped. Color: Yellowish-green (a color in between RHS N144A and RHS 145C) and purplish-red margins (RHS N77B) toward the tip.

*Petals.*—Arrangement: Open/free. Shape: Semi-circular. Apex: Slightly emarginated asymmetric. Margin: Moderately undulated. Length (from base to tip): 40.0 mm to 42.0 mm. Width: 40.0 mm to 42.0 mm. Position of the broadest part of the petal: Toward the base. Color (when fully opened): Upper surface: Basic color: Light greenish-yellow (RHS 1D). Over color: Greenish-white center (RHS 155C) and dark purplish-pink shade (RHS 186C) toward margins. Lower surface: Basic color: Light greenish-yellow (RHS 1D). Over color: Purplish-pink shade (RHS 186D). Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal.*—Shape: Elliptic. Apex: Emarginated symmetric. Margin: Weakly undulated. Length (from base to tip): 41.0 mm to 43.0 mm. Width: 28.0 mm to 30.0 mm. Position of the broadest part of the dorsal sepals: At the middle. Color (when fully opened): Upper surface: Basic color: Light greenish-yellow (RHS 160C). Over color: Yellow-green over-color (RHS 150C) and dark purplish-pink shade (RHS 186C) toward margins. Lower surface: Basic color: Light greenish-yellow (RHS 160C). Over color: Yellow-green (RHS N144D) at the middle and purplish-pink shade (RHS 186D) toward margin. Number of spots and stripes on the dorsal sepals (upper surface): None. Color of spots and stripes on the dorsal sepals (upper surface): Not applicable. Density of netting of the dorsal sepals (upper surface): None. Color of the netting: Not applicable.

*Lateral sepals.*—Shape: Ovate. Apex: Obtuse symmetric. Margin: Weakly undulated. Length (from base to tip): 41.0 mm to 43.0 mm. Width: 26.0 mm to 28.0 mm. Position of the broadest part of the lateral sepals: At the base. Color (when fully opened): Upper surface: Basic color: Yellow-green (RHS 150C). Over color: Purplish-pink shade (a color in between RHS 186C and RHS 186D) toward margins. Lower surface: Basic color: Yellowish-green (a color in between RHS N144A and RHS 145C). Over color: Purplish-pink shade (a color in between RHS 186B and RHS 186C) toward margins. Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum (lip).*—Whiskers: Present. Length of whiskers: 6.0 mm to 8.0 mm. Color of whiskers: White (RHS NN155C). Pubescence on the lip: Absent.

*Lateral lobe.*—Shape: Type IV (as described in the International Union for the Protection of New Varieties of Plants (UPOV) Test Guidelines for *Phalaenopsis*); weakly spatulate. Margin: Moderately undulated. Length: 16.0 mm to 18.0 mm. Width: 8.0 mm to 10.0 mm. Color: Upper surface: Yellow (RHS 13B); dotted (RHS 183B) at the base; yellow (RHS 14B) toward margin on one side; white (RHS NN155C) toward the other side and tip. Lower surface: White (RHS NN155C); yellow (RHS 14B) on one side. Number of spots, dots, and stripes on the lateral lobe: Medium dots. Color of spots, dots, and stripes on the lateral lobe: RHS 183B. Density of netting of the lateral lobe: None. Color of the netting: Not applicable.

*Apical lobe.*—Shape: Trullate. Margin: Entire. Length: 20.0 mm to 22.0 mm. Width: 19.0 mm to 21.0 mm. Color: Upper surface: Very small dark reddish-orange dots (RHS 175B) and yellow (RHS 12A) at the base; white (RHS NN155C) toward whiskers. Lower surface: Dark reddish-orange (RHS 175B) and yellow (RHS 12B) at the base and toward wings; very light purple (RHS 75A) at the middle from base and white (RHS NN155C) toward whiskers. Number of spots, dots, and stripes on the apical lobe: Many very small dots. Color of spots, dots, and stripes on the apical lobe: RHS 175B. Density of netting of the apical lobe: None. Color of the netting: Not applicable.

*Callus.*—Average size: Small. Height: 4.0 mm to 5.0 mm. Length: 3.0 mm to 4.0 mm. Width: 3.0 mm to 4.0 mm. Color: Yellow (RHS 13B); light greenish-yellow (RHS 3D) on sides; dotted (RHS 18B).

Reproductive organs:

*Column.*—Length: 8.0 mm to 10.0 mm. Diameter: 3.8 mm to 4.3 mm. Color: White (RHS NN155C).

*Pollinia.*—Quantity: 2. Diameter: 0.8 mm to 1.0 mm. Color: Orange-yellow (RHS 17A).

*Ovary.*—Length: 12.0 mm to 14.0 mm. Diameter: 1.9 mm to 2.2 mm.

*Pedicel.*—Length: 33.0 mm to 35.0 mm. Diameter: 2.3 mm to 2.8 mm. Color: Yellow-green (RHS 145A) and lighter yellow-green (RHS 145C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA1734832' differs from the female parent plant '33350-01' (unpatented) in that 'PTHA1734832' has trullate apical lobes, flowers with a shaded pattern, and whiskers, whereas '33350-01' has rhombic apical lobes, flowers with a spotted pattern at the base, and no whiskers.

'PHA1734832' differs from the male parent plant '42375-01' (unpatented) in that 'PTHA1734832' has trullate apical lobes and flowers with a main color of light greenish-yellow and having a shaded pattern, whereas '42375-01' has triangular apical lobes and flowers with a main color of purplish-pink and having a striped and center pattern.

'PHA1734832' is most similar to the commercial *Phalaenopsis* plants named 'PHALGOBI' (U.S. Plant Pat. No. 31,804) and 'PHALGLAZAL' (U.S. Plant Pat. No. 29,909). 'PHA1734832' differs from the commercial variety 'PHALGOBI' in that 'PHA1734832' has trullate apical lobes and flowers with a shaded pattern, whereas 'PHALGOBI' has triangular apical lobes and flowers with an even pattern. Additionally, 'PHA1734832' has narrower leaves and narrower petals than 'PHALGOBI'.

'PHA1734832' differs from the commercial variety 'PHALGLAZAL' in that 'PHA1734832' has trullate apical lobes, white whiskers, and flowers with a shaded pattern, whereas 'PHALGLAZAL' has rhombic apical lobes, light brown whiskers, and flowers with a dotted pattern. Additionally, 'PHA1734832' has narrower petals than 'PHALGLAZAL'.

I claim:

1. A new and distinct variety of *Phalaenopsis* plant named 'PHA1734832', substantially as described and illustrated herein.

* * * * *